United States Patent [19]
Radcliffe et al.

[11] Patent Number: 5,168,865
[45] Date of Patent: Dec. 8, 1992

[54] KNEE BRACE WITH PIVOT LOCK

[75] Inventors: Charles Radcliffe, Lafayette; Steve Lamb, Hayward, both of Calif.

[73] Assignee: Orthopedic Systems, Inc., Hayward, Calif.

[21] Appl. No.: 696,208

[22] Filed: May 6, 1991

[51] Int. Cl.$^5$ .............................................. A61F 5/00
[52] U.S. Cl. ...................................... 602/16; 602/26
[58] Field of Search ................. 128/80 F, 80 C, 80 R, 128/88, 77

[56] References Cited

U.S. PATENT DOCUMENTS

| | | | |
|---|---|---|---|
| 3,901,223 | 8/1975 | May | 128/80 f |
| 4,523,585 | 6/1985 | Lamb et al. | |
| 4,723,539 | 2/1988 | Townsend | |
| 4,773,404 | 9/1988 | Townsend | |
| 4,821,707 | 4/1989 | Audette | 128/80 C |
| 4,844,057 | 7/1989 | Hoy | 128/80 C |
| 4,886,054 | 12/1989 | Castillo et al. | 128/80 C |
| 4,940,044 | 7/1990 | Castillo | 128/80 C |
| 4,961,416 | 10/1990 | Moore et al. | |
| 5,018,514 | 5/1991 | Grood et al. | 128/80 C |

Primary Examiner—Richard J. Apley
Assistant Examiner—Lynne A. Reichard
Attorney, Agent, or Firm—Bielen, Peterson & Lampe

[57] ABSTRACT

A knee brace utilizing first and second brace members and first and second elements which are interlinked to one another. The first and second brace members are adapted for attachment to the femoral and tibial regions of the leg. The first and second brace members each include a first and second second portion. The first element pivotally connects to the first brace member at a first pivot and to the second brace member at a second pivot. The second brace member also pivotally connects to the second element at a third pivot. The second element pivotally connects to the first brace member at a fourth pivot. The first and second elements may sandwich or bracket the first and second brace members, which are generally positioned in a coplanar relationship. Position of the first brace member relative to the second brace member permits selected translation between these brace members.

16 Claims, 2 Drawing Sheets

KNEE BRACE WITH PIVOT LOCK

BACKGROUND OF THE INVENTION

The present invention relates to a novel brace mechanism which is especially adaptable to bracing the knee joint.

Knee braces have been employed to support the knee of a patient after knee surgery or subsequent to a fracture of the tibia or femur. Recently it has been found that the use of a knee brace which allows limited rotation of the knee reduces joint stiffness and atrophy of the muscles of the leg surrounding the knee joint. It has long been recognized, that the knee joint is a polycentric system i.e. the knee pivots on more than one pivot axis during movement from flexion to extension.

Reference is made to U.S. Pat. No. 4,523,585 showing a four bar linkage mechanism which achieves a polycentric motion that generally follows the actual motion of the human knee. Among the recently recognized movements of the human knee is the translational motion, or "drawer", between the tibia and femur. Reference is made to U.S. Pat. No. 4,961,416 which devised a unique bar apparatus to limit such translational motion during extension of a braced knee.

Although the brace device described in U.S. Pat. No. 4,961,416 successfully controlled translation or "drawer", it has been recently hypothesized that the medial portion of the knee translates differently than the lateral portion of the knee. For example, it is believed that the medial portion of the knee may translate on the average of 8 mm while the lateral portion of the knee may translate up to 20 mm. Thus, it is important to incorporate such differential translation into a knee brace in order to closely follow the natural kinematic motion of the knee.

U.S. Pat. Nos. 4,723,539 and 4,773,404 illustrate a linkage which permits sliding rotation between the femur and tibia by the use of cam slots and cam pin followers. Such linkage is subject to constant friction and wear, and generates excessive noice during movement.

A brace which solves the problems found in the prior art would be a great advance in the orthopedic field of medicine.

SUMMARY OF THE INVENTION

In accordance with the present invention a novel and useful knee brace is herein provided.

The brace of the present invention utilizes first and second brace members each including first and second portions. The first portion of the first brace member would lie closest to the first portion of the second brace member. The brace mechanism also encompasses a first element in the form of a bar or the like which rotatably pivots relative to the first brace member. The first element also rotates on a second pivot relative to the second brace member. A second element rotatably pivots between the second brace member and the second element. Finally, the second element also pivots on a fourth pivot permitting rotation between the second element and the first knee brace member. The first pivot is located toward the second portion of the first brace member relative to the fourth pivot, while the second pivot is located toward the second portion of the second brace member relative to the third pivot. The first and second elements may be stacked relative to the first and second brace members. In this regard, the first brace member may include a cavity such that the second element would lie within the cavity. Also, the cavity permits the first and second brace members to lie essentially in a coplanar relationship.

Stop means may also be included in the present invention for arresting movement between the first and second brace members. Such stop means may take the form of an edge on the first portion of the first brace member which meets an edge of the first portion of the second brace member. The edges of the first and second brace members are capable of contacting one another during relative movement between the same. The edge of the second brace member may also serve as a contact surface for a guide which is located on the edge of the first brace member. The guide may be formed of resilient material to bias movement of the second brace member in a translation direction. A cushion may also be employed to at least partially interrupt the contact between the edge portions of the first and second brace members.

The rotation of the first element relative to the second element may be limited to simple rotation about the coaxial second and fourth pivots during one portion of the movement between the first and second brace members. Further, such movement may be expanded to include rotation around all four pivots during another portion of the relative movement between the first and second brace members. In the later case, a translation or "drawer" action would also take place between the first and second brace members. Sizing of the first and second elements creates this natural kinematic pivot lock, permitting translation without the use of a less efficient slot or cam mechanism shown in the prior art. The stop means prior described would also arrest the translational movement between the first and second brace members.

It should be realized that the first and second elements of the knee brace of the present invention may be sized to predetermine a translational distance traveled between the first and second brace members. Also this sizing of the brace members and elements necessarily predetermines the degree of rotation prior to the mode of combined rotation and translation. Thus, individual braces of the present invention may be placed on the medial and lateral portions of the knee to permit differential translation.

It may be apparent that a novel and useful knee brace has been described.

It is therefore an object of the present invention to provide a knee brace which possesses a kinematic pivot locking mechanism which prevents translational movement between a first and second brace member only during a portion of the rotational movement therebetween.

It is another object of the present invention to provide a knee brace which very closely mimics a natural motion of the human knee.

Another object of the present invention is to provide a knee brace which is compact and reliable in allowing the human knee to move in a normal manner.

Yet another object of the present invention is to provide a knee brace which utilizes at least a pair of linkages placed on the lateral and medial portions of the knee, each linkage permitting a selective translational movement between the first and second brace members and, thus, the femur and tibia of the human knee.

Another object of the present invention is to provide a knee brace which greatly eliminates friction wear and noise found in the prior art slot and cam pin structure.

The invention possesses other objects and advantages especially as concerns particular characteristics and features thereof which will become apparent as the specification continues.

For a better understanding of the invention reference is made to the following detailed description of the preferred embodiments thereof which should be referenced to the hereinabove described drawings.

DESCRIPTION OF THE PREFERRED EMBODIMENTS

Various aspects of the present invention will evolve from the following detailed description of the preferred embodiments which should be taken along with the prior described drawings.

Figure 3:
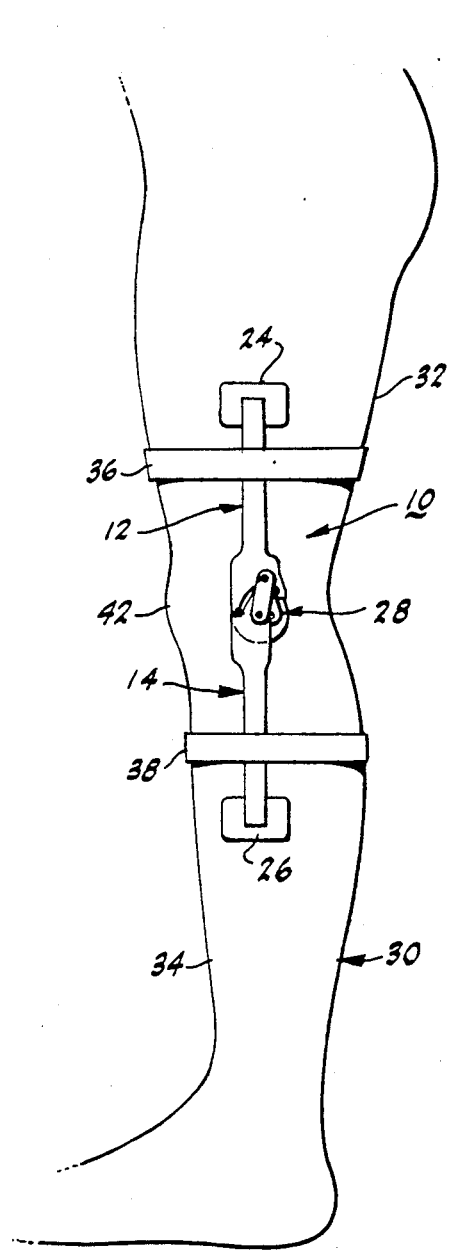
FIG. 3 is a side elevational view of the brace of the present invention in place on a human knee joint.
Figure 2:
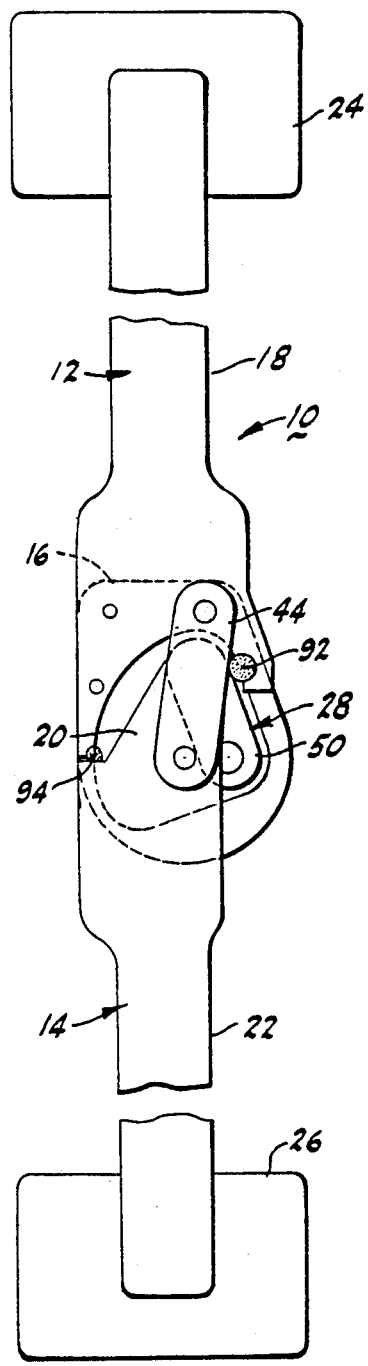
FIG. 2 is a side elevational view of the brace of the present invention with portion of the first and second brace members depicted in broken configuration.
Figure 1:
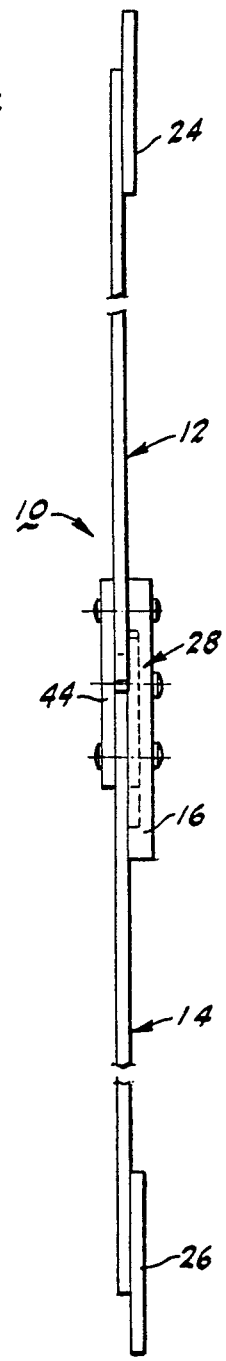
FIG. 1 is a rear elevational view of the brace of the present invention with portions of the first and second brace member shown in broken configuration.

The invention as a whole is depicted in the drawings by reference character 10. The brace 10 includes as one of its elements a first brace member 12 and a second brace member 14, FIG. 1. First brace member 12 includes a first portion 16 and a second portion 18. Similarly, second brace member 14 includes a first portion 20 and a second portion 22. The second portions 18 and 22 of first and second brace members 12 and 14 are used in conjunction with pads 24 and 26, respectively, FIG. 2. Brace 10 includes a linkage mechanism 28 which very closely mimics the movement of the human knee joint which will be described in greater detail hereafter. Turning to FIG. 3, it may be observed that brace 10 has been fixed to human left leg 30 having a femoral portion 32 and a tibial portion 34. Thus, first brace member second portion 18 is fixed via a strap 36 to the femoral portion 32 of leg 30, and second brace member 14 second portion 22 has been fixed to tibial portion 34 of leg 45 via strap 38. It should be realized, that other means may be employed to fix brace 10 to leg 30. Linkage mechanism 28 lies at the lateral portion of knee 42 of left leg 30.

Figure 4:
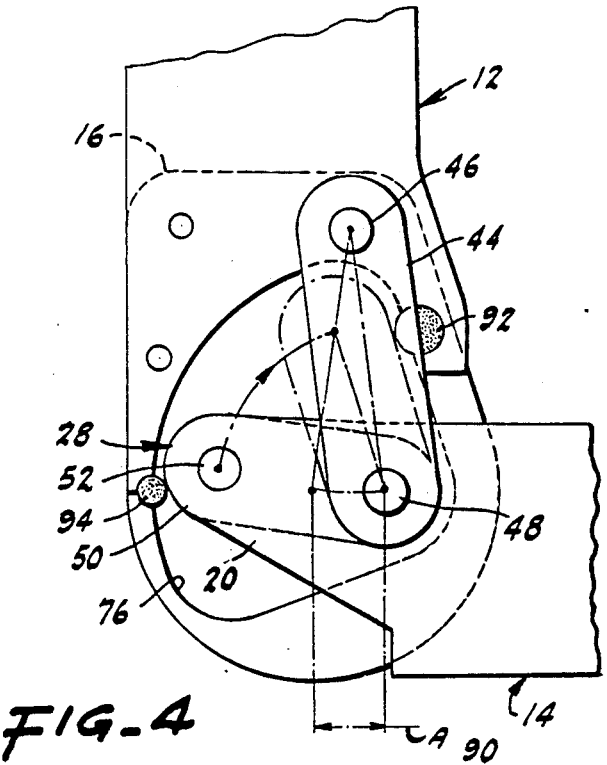
FIG. 4 is a side elevational view of the knee brace of the present invention in a position simulating 90° flexion of the knee joint.

Turning now to FIG. 4, it may be observed that linkage 28 includes a first spanning element or bar 44 which pivotally attaches to the first brace member 12 at first pivot 46. First element 44 pivotally attaches to second brace member 14 at second pivot 48. Second spanning element or bar 50 pivotally connects to second brace member 14 at third pivot 52. Second spanning element 50 also pivotally connects to first brace member 12 at fourth pivot 54, most clearly shown in FIG. 6. It may be apparent from FIG. 7, that first, second, third and fourth pivots, 46, 48, 52, and 54 take place around axes 56, 58, 60, and 62, respectively. Axes 58 and 62 are coincident during a portion of the movement between first and second brace members 12 and 14. Such relationship is best shown on FIG. 7. Pin 64 connects first element 44 to first brace member 12, as well as terminal body 66 to bar 68 which constitutes first portion 16 of first brace member 12. Rivet 70 serves to rotatably pin first portion 20 of second brace member 14 to second element 50. Finally, pins 72 and 74 rotatably fasten first element 44 to second brace member 14 and second element 50 to first brace member 12 at terminal body 66, respectively. It should be noted that terminal body 66 includes a cavity 76 which encompasses second element 50 and a portion of second brace member 14. Thus, first and second brace members 12 and 14 are essentially coplanar and lie within plane 78, FIG. 7. Second element 50 positions within cavity 76 and combines with first element 44 to sandwich second brace member which also extends a certain distance into cavity 76. Plurality of spacers 80 of lubricating material, such as polymeric plastic, separate first and second brace members 12 and 14 and first and second elements 44 and 50 at first, second, third, and fourth pivots 44, 48, 52, and 54, respectively, FIG. 7.

Figure 6:
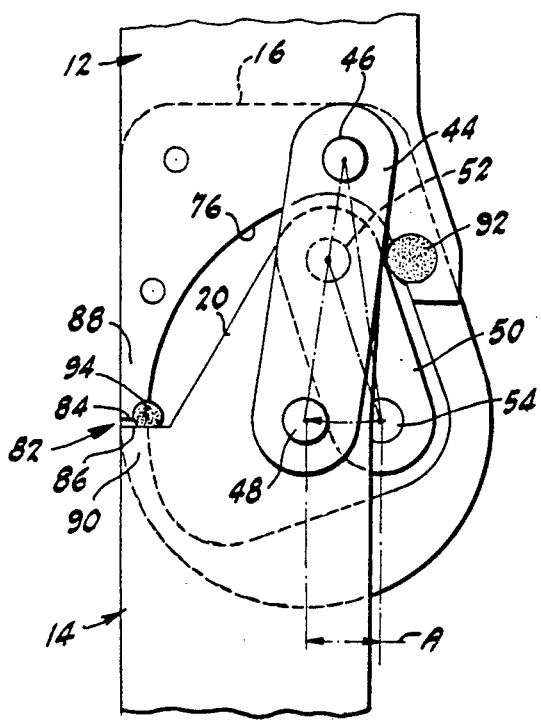
FIG. 6 is a side elevational view of the brace of the present invention simulating full extension of the knee.
Figure 7:
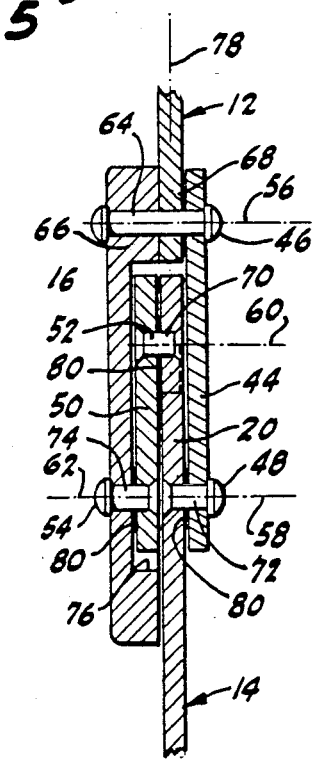
FIG. 7 is a sectional view taken along line 7—7 of FIG. 5.

Stop means 82 is depicted in FIG. 6 as including edges 84 and 86 at shoulders 88 and 90 of first and second brace members 12 and 14, respectively. Edge portions 84 and 86 are capable of contacting one another at shoulders 88 and 90, FIG. 6. Guide 92 in the form of a resilient disk connects to first portion 16 of first brace member 12 and is capable of riding on edge portion 86 of first portion 20 of second brace member 14. Resilient disk 92 thus serves as a means for biasing second brace member in its extension by rotation in a clockwise direction, FIGS. 4–6. In addition, a resilient disk 94 is connected to first portion 16 of first brace member 12. Resilient disk 94 would be positioned at the meeting place of edges 84 and 86 at shoulders 88 and 90 to cushion the contact, therebetween.

Figure 5:
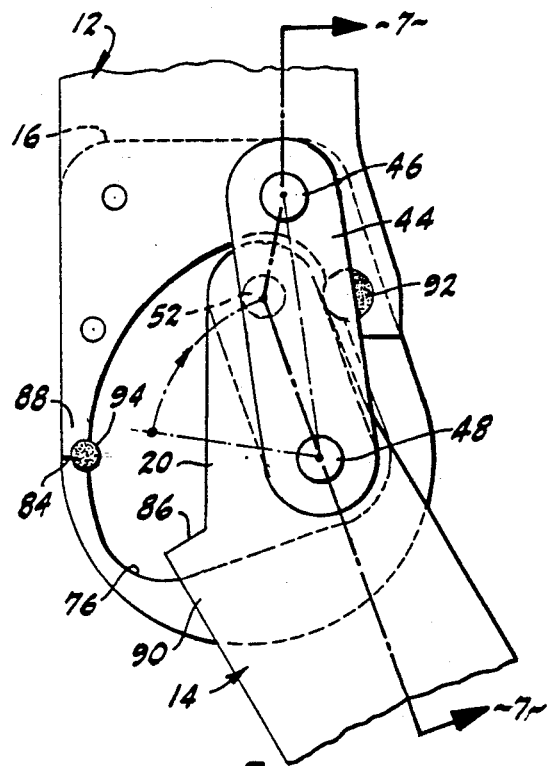
FIG. 5 is a side elevational view of the brace of the present simulating position of 30° from full extension of the knee.

In operation, brace 10 is fastened a leg such as left leg 30 depicted in FIG. 3 by use of straps 36 and 38. A similar brace mechanism to mechanism 10 also fastens on the medial side of leg 30 (not shown). Turning to FIGS. 4–6 it may be seen, when leg 30 is flexed to 90°, the linkage 28 will take the configuration shown in FIG. 4. Further extension of leg 30 will result in the pivotal movement between first and second brace members 12 and 14 at second and fourth pivots 48 and 54, respectively. With reference to FIG. 5, it is shown that extension of brace 10 has taken place to within 30° of full extension. During such travel from the position shown in FIG. 4 to the position shown in FIG. 5, linkage 28 has locked the rotational movement of first element 44 about first pivot 46. Further extension of leg 30 and second brace member 14 to the position shown in FIG. 6 will result in the pivoting of first element 44 about the first pivot 46 and pivoting of second element 50 about third pivot 52. The resulting movement of first element 44 permits second brace member 14 to translate a certain distance shown in FIG. 6 as distance "A". Guide 92 initiates such translation. In other words, second pivot 48 has moved from immediately above fourth pivot 54, (where axis 58 is coincident with axis 62) FIGS. 4 and 5 to a position to the left of pivot 54 in FIG. 6. It has been found that adjusting the distance along the first and second elements 44 and 50, as well as the size of the cavity 76, predetermines the translation distance "A" and the angle at which translation begins. Stop means 82 prevents further movement between first and second brace members 16. Resilient disk 94 cushions stop means 82 in its function. The following is a table representing the distances between pivot points on first and second elements 44 and 50 determining the translation distance "A" on FIG. 6.

TABLE I

| | Center to center distance between first pivot 46 and second pivot 48 along first element 44 | center to center distance between third pivot 52 and fourth pivot 54 along second element 50 | translation distance "A" (FIG. 6) | translation initiation angle from full extension between first and second brace members 12 and 14 |
|---|---|---|---|---|
| 1. | 18.0 mm | 12.0 mm | 6 mm | 25° |
| 2. | 25.0 mm | 15.0 mm | 8 mm | 25° |
| 3. | 30.0 mm | 20.0 mm | 10 mm | 25° |
| 4. | 25.0 mm | 15.0 mm | 6 mm | 20° |
| 5. | 30.0 mm | 20.0 mm | 8 mm | 20° |
| 6. | 40.0 mm | 30.0 mm | 10 mm | 20° |

It should be observed that a linkage mechanism 28 with the translation distance of 8 mm may be placed on, for example, the medial side of left leg 30 and a linkage 28 having a translation distance of 20 mm may be placed on the lateral side portion of leg 30, depending on the particular circumstances. As previously stated it is believed that a natural motion of the knee utilizes a differential translation between the medial and the lateral portions of the knee.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

We claim:

1. A knee brace comprising;
   a. a first brace member including means for holding said first brace member to the femoral portion of the leg said first brace member further including a first portion and a second portion;
   b. a second brace member including means for holding said second brace member to the tibial portion of the leg said second brace member further including a first portion and a second portion;
   c. a first element including a first pivot permitting rotation between said first element and said first brace member, and a second pivot permitting rotation between said first element and said second brace member; and
   d. a second element including a third pivot permitting rotation between said second brace member and said second element, and a fourth pivot permitting rotation between said second element and said first knee brace member, said first pivot being located along said first brace member a selected distance from said fourth pivot and said second pivot being located along said second brace member a selected distance from said third pivot, to prevent rotation of said first brace member relative to said first element during a portion of said rotation of said second brace member relative to said first element.

2. The brace of claim 1 in which said first and second element at least partially sandwich said first brace member.

3. The brace of claim 1 in which said first brace member includes a cavity and said second element lies within said cavity.

4. The brace of claim 1 in which said first and second brace members each lie within a plane.

5. The brace of claim 1 which further includes stop means for arresting movement between said first and second brace member.

6. The brace of claim 5 in which said stop means includes a first edge on said first portion of said first brace member and a edge on said first portion of said second brace member, said edges of said first and second members being capable of contacting one another.

7. The brace of claim 1 in which said first and second elements are sized to limit rotation of said first element and said first brace member about said first pivot during rotation of said first element relative to said second brace member about said second pivot.

8. The brace member of claim 7 in which said limit rotation of said first element relative to said first brace member about said first pivot includes prevention of rotation of said first element relative to said second brace member about said second pivot during a portion of said rotation of said first element relative to said first brace member about said first pivot.

9. The brace of claim 8 which further includes stop means for arresting movement between said first and second brace members.

10. The brace of claim 9 in which said stop means further includes means for arresting rotation of said first element relative to said second brace member about said second pivot.

11. The brace of claim 10 in which said stop means includes a first edge on said first portion of said first brace member and a edge on said first portion of said second brace member, said edges of said first and second members being capable of contacting one another.

12. The brace of claim 1 which additionally comprises means for biasing movement of said second brace member relative to said first brace member.

13. The brace of claim 12 which said means for biasing comprises a guide on said first brace member contacting said second brace member during relative motion between said first and second brace members.

14. The brace of claim 12 in which said guide is positioned on an edge portion of said first brace member, and said guide contacts an edge portion of said second brace member.

15. The brace of claim 11 which additionally comprises a cushion selectively fixed to said first and second brace members, said cushion being located to absorb the stopping force exerted by said stop means.

16. The brace of claim 15 in which said first and second brace members include edges on said first portions thereof capable of contacting one another, and said cushion is positioned to at least partially interupt said contact between said edges of said first and second brace members.

* * * * *